United States Patent
Simoes et al.

(10) Patent No.: US 11,850,158 B2
(45) Date of Patent: Dec. 26, 2023

(54) ORTHOPEDIC SURGICAL IMPLANT DEVICE WITH POROUS MATERIAL AND FLUID CHANNELS FOR CLEANING THE POROUS MATERIAL

(71) Applicant: HOWMEDICA OSTEONICS CORP., Mahwah, NJ (US)

(72) Inventors: Vincent Abel Maurice Simoes, Locmaria Plouzané (FR); Florence Delphine Muriel Maillé, Locmaria Plouzané (FR); Sergii Poltaretskyi, Plougonvelin (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 30 days.

(21) Appl. No.: 17/242,004

(22) Filed: Apr. 27, 2021

(65) Prior Publication Data

US 2021/0369465 A1 Dec. 2, 2021

Related U.S. Application Data

(60) Provisional application No. 63/029,932, filed on May 26, 2020.

(51) Int. Cl.
*A61F 2/40* (2006.01)
*A61F 2/30* (2006.01)

(52) U.S. Cl.
CPC .......... *A61F 2/4081* (2013.01); *A61F 2/3094* (2013.01); *A61F 2002/30011* (2013.01);
(Continued)

(58) Field of Classification Search
CPC .......... A61F 2/4081; A61F 2002/30011; A61F 2002/30578; A61F 2002/30985; A61F 2/3094; A61F 2/28
See application file for complete search history.

(56) References Cited

U.S. PATENT DOCUMENTS 6,270,529 B1 * 8/2001 Terrill-Grisoni ...... A61F 2/3804
623/20.11
7,715,602 B2 5/2010 Richard
(Continued)

FOREIGN PATENT DOCUMENTS

EP 0814731 B1 8/2002
EP 2323587 B1 8/2016
(Continued)

OTHER PUBLICATIONS

Brochure entitled Important Information (with Cleaning and Sterilization Instructions), by DePuy Synthes, downloaded from http://synthes.vo.llnwd.net/o16/LLNWMB8/INT%20Mobile/Synthes%20International/elFU-EMEA/023827/023827AMeng.pdf on Nov. 2, 2021, originally SE_023827 AM Apr. 2020, 11 pp.
(Continued)

*Primary Examiner* — Jacqueline Woznicki
(74) *Attorney, Agent, or Firm* — Shumaker & Sieffert, P.A.

(57) ABSTRACT

This disclosure describes a surgical implant device comprising a body that includes a porous material forming at least a portion of the body, wherein the porous material is configured to promote bone ingrowth and is porous to a fluid. In addition, one or more fluid channels are formed in the body. The one or more fluid channels are arranged to define a fluidic path that exits into the porous material.

27 Claims, 11 Drawing Sheets

(52) U.S. Cl.
CPC ............ *A61F 2002/30578* (2013.01); *A61F 2002/30691* (2013.01); *A61F 2002/30985* (2013.01)

(56) References Cited

U.S. PATENT DOCUMENTS

| | | | |
|---|---|---|---|
| 7,857,821 B2 | 12/2010 | Couture et al. | |
| 8,147,496 B2 | 4/2012 | Couture et al. | |
| 8,506,645 B2 | 8/2013 | Blaylock et al. | |
| 9,775,680 B2 | 10/2017 | Bojarski et al. | |
| 10,426,549 B2 | 10/2019 | Kehres et al. | |
| 10,716,674 B2* | 7/2020 | Jurick | A61F 2/0811 |
| 10,722,374 B2* | 7/2020 | Hodorek | A61F 2/4081 |
| 10,881,462 B2 | 1/2021 | Heavener et al. | |
| 2005/0203630 A1* | 9/2005 | Pope | A61F 2/30767 623/20.28 |
| 2010/0042213 A1* | 2/2010 | Nebosky | A61B 17/60 606/280 |
| 2010/0274359 A1* | 10/2010 | Brunnarius | A61F 2/30734 623/19.13 |
| 2013/0053968 A1 | 2/2013 | Nardini et al. | |
| 2013/0211539 A1* | 8/2013 | McDaniel | A61F 2/28 623/23.53 |
| 2016/0199190 A1 | 7/2016 | Sharifi-Mehr et al. | |
| 2016/0199193 A1 | 7/2016 | Willis et al. | |
| 2018/0071104 A1* | 3/2018 | Kovacs | A61F 2/30734 |
| 2018/0280139 A1 | 10/2018 | Jones et al. | |
| 2019/0167433 A1* | 6/2019 | Allen | A61F 2/30721 |
| 2021/0000568 A1 | 1/2021 | Renne et al. | |

FOREIGN PATENT DOCUMENTS

| | | | |
|---|---|---|---|
| KR | 101758853 B1 | 7/2017 | |
| WO | 2018183809 A1 | 10/2018 | |

OTHER PUBLICATIONS

Brochure entitled "Tornier SIMPLICITI™ Shoulder System," by Wright Medical Group, downloaded from https://www.wright.com/products-upper/simpliciti-shoulder-arthroplasty-system on May 1, 2020, 1 pp.

Brochure entitled "Torier SIMPLICITI™ Shoulder System," by Wright Medical Group, downloaded from https://www.wright.com/products-upper/simpliciti-shoulder-arthroplasty-system on Nov. 2, 2021, 6 pp.

Brochure entitled "Tornier, SIMPLICITI™ Shoulder System—Surgical Technique (CAW-7656_EN_LR_LE)," by Wright Medical Group, downloaded from https://www.wrightemedia.com/ProductFiles/Files/PDFs/CAW-7656_EN_LR_LE.pdf on Nov. 2, 2021, dated Jan. 14, 2016, 24 pp.

"Cleaning internal cavities and channels," from Formlabs, downloaded from https://support.formlabs.com/s/article/Cleaning-Internal-Cavities-and-Channels?language=en_US on Apr. 8, 2021, originally published Aug. 12, 2018, 3 pp.

"Development in cleaning 3D printed medical implants launched," from MED-TECH Innovation News, downloaded from https://www.med-technews.com/news/development-in-cleaning-3d-printed-medical-implants-launched/ on Apr. 8, 2021, originally published Feb. 5, 2020, 10 pp.

Basalah et al., "Characterizations of additive manufactured porous titanium implants," Journal of Biomedical Materials Research Part B Applied Biomaterials, vol. 100B, No. 7, Aug. 2012, 10 pp.

Boissonnat, J.D., "Shape Reconstruction from Planar Cross Sections," Computer Vision, Graphics, and Image Processing, vol. 44, No. 1, Oct. 1988, 29 pp.

Goh et al., "Fabrication of 3D Microfluidic Channels and In-Channel Features Using 3D Printed, Water-Soluble Sacrificial Mold," Macromolecular Materials and Engineering, vol. 303, No. 3, Jan. 2018, 9 pp.

Gordeev et al., "Improvement of quality of 3D printed objects by elimination of microscopic structural defects in fused deposition modeling," PLoS ONE, vol. 13, No. 6, Jun. 2018, 19 pp.

Marker et al., "Contour-Based Surface Reconstruction using Implicit Curve Fitting, and Distance Field Filtering and Interpolation," Volume Graphics, Jan. 2006, 9 pp.

Nguyen et al., "A new segmentation method for MRI images of the shoulder joint," Fourth Canadian Conference on Computer and Robot Vision (CRV'07), May 2007, 8 pp.

Zeldovich, L., "3D Printing Overcoming Biocompatibility Challenge," The American Society of Mechanical Engineers, Feb. 2020, 8 pp.

Zou et al., "Novel exploration of customized 3D printed shoulder prosthesis in revision of total shoulder arthroplasty—A case report," Medicine (Baltimore), vol. 97, No. 47, Nov. 2018, 7 pp.

Extended Search Report from counterpart European Application No. 21171007.4, dated Oct. 15, 2021, 10 pp.

Response to Extended Search Report dated Oct. 15, 2021, from counterpart European Application No. 21171007.4 filed Mar. 14, 2022, 18 pp.

Extended Search Report from counterpart European Application No. 21171007.4 dated May 2, 2023, 7 pp.

Response to Extended Search Report dated May 2, 2023, from counterpart European Application No. 21171007.4 filed Jul. 31, 2023, 10 pp.

\* cited by examiner

ORTHOPEDIC SURGICAL IMPLANT DEVICE WITH POROUS MATERIAL AND FLUID CHANNELS FOR CLEANING THE POROUS MATERIAL

This application claims the benefit of U.S. Provisional Application 63/029,932, filed May 26, 2020, the entire content of which is incorporated herein by reference.

BACKGROUND

Surgical joint repair procedures involve repair and/or replacement of a damaged or diseased joint. For example, a surgical joint repair procedure, such as joint arthroplasty as an example, involves replacing the damaged joint with a prosthetic, or set of prosthetics, that is implanted into the patient's bone. In many cases, orthopedic implant devices may include porous material designed to promote bone ingrowth to secure the implant at a desired location.

Proper selection of a prosthetic that is appropriately sized and shaped and proper positioning of that prosthetic to ensure an optimal surgical outcome can be challenging. To assist with positioning, the surgical procedure often involves the use of surgical instruments to control the shaping of the surface of the damaged bone and cutting or drilling of bone to accept the prosthetic. In some cases, 3D printing techniques may be used to create implants that match the shape of patient anatomy, which can reduce or eliminate the need to resurface the patient's bone at the location of the implant.

SUMMARY

This disclosure describes an orthopedic surgical implant device that includes fluid flush channels formed in the surgical implant device, in order to facilitate cleaning of the device after manufacturing the device. In some examples, the orthopedic surgical implant device is a patient-specific device that is shaped to match the anatomy of a specific patient. A three-dimensional (3D) printing or other additive manufacturing process (such as a direct metal laser sintering (DMLS) process) may be used to manufacture the device based on images of the patient's anatomy.

One or more surfaces of the orthopedic surgical implant device may comprise a porous material that promotes bone ingrowth after implantation onto a patient's bone. In some examples, the orthopedic surgical implant device comprises a baseplate associated with an orthopedic implant, and the baseplate may include a porous material that promotes bone ingrowth after implantation onto a patient's bone. A bottom surface of the orthopedic surgical implant device may include the porous material and the bottom surface may be designed to conform to patient-specific anatomy (e.g., the shape of a patient's bone at the location of implant).

In accordance with this disclosure, one or more fluid channels are formed in the orthopedic surgical implant device to improve a post-manufacturing cleaning process of the orthopedic surgical implant device. In particular, fluid can be flushed into the channels to clean the porous material of the orthopedic surgical implant device. For instance, fluid passing through the one or more channels may exit the one or more fluid channels into the porous material and subsequently exit the implant device. In this way, the interior region of the orthopedic surgical implant device and the pores of the porous material can be more thoroughly cleaned, prior to the device being implanted in a patient.

In some examples, this disclosure describes a surgical implant device comprising a body that includes a porous material forming at least a portion of the body, wherein the porous material is configured to promote bone ingrowth and is porous to a fluid. In addition, one or more fluid channels are formed in the body. The one or more fluid channels are arranged to define a fluidic path that exits into the porous material In other examples, this disclosure describes a method that comprises printing a surgical implant device, such as via a DMLS process or another 3D printing process. The surgical implant device may be printed to define a body including a porous material forming at least a portion of the body, wherein the porous material is configured to promote bone ingrowth and is porous to a fluid. In addition, the surgical implant device may be printed to define one or more fluid channels formed surgical implant device, wherein the one or more channels define a fluidic path that exits into the porous material. After printing the surgical implant device, the method may further comprise flushing fluid (e.g., water and/or possibly a cleaning agent) into the one or more fluid channels and into the porous material. In this way, the surgical implant device can be cleaned in a more thorough way than conventional surface cleaning, which is desirable.

The details of various examples of the disclosure are set forth in the accompanying drawings and the description below. Various features, objects, and advantages will be apparent from the description, drawings, and claims.

DETAILED DESCRIPTION

Figure 1:
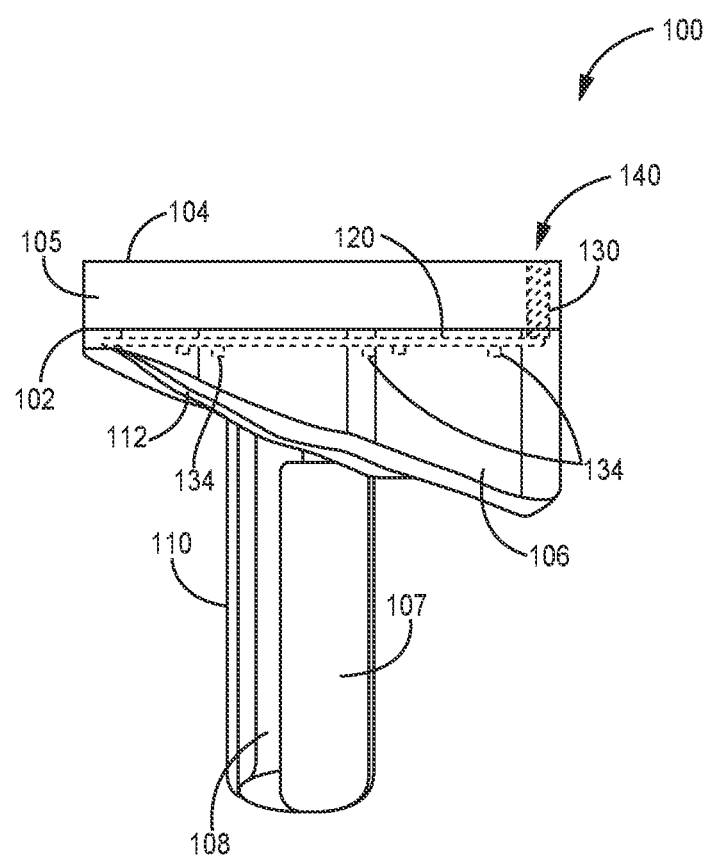
FIG. 1 is a conceptual side view of an example orthopedic implant device consistent with this disclosure.

This disclosure describes an orthopedic surgical implant device that includes fluid flush channels formed in the surgical implant device, in order to facilitate cleaning of the device after manufacturing the device. As one example, the orthopedic surgical implant device may comprise a baseplate designed to be implanted in the glenoid cavity of a scapula bone of a patent. A glenoid plate or a glenoid sphere may be attached to the baseplate, and the baseplate may be designed to receive such attachments. A glenoid plate, for example, may be used for an anatomical shoulder arthroplasty, and a glenoid sphere, for example, may be used for a reverse anatomical shoulder arthroplasty. Although details of this disclosure are described in the context of baseplates for orthopedic shoulder implant devices, the techniques and devices described herein may applied to a wide variety of other baseplates or for other orthopedic implants, e.g., used for arthroplasty of other joints. The techniques may also be applied to screws, plates, or any devices or elements that include porous material configured to promote bone ingrowth and designed for implantation onto the bone of a patient.

As described herein, an orthopedic surgical implant device may be designed and manufactured to include one or more fluid flush channels formed in the orthopedic surgical implant device. The fluid flush channels are arranged to facilitate cleaning of the device after manufacturing of the device. In particular, the one or more fluid flush channels define a fluidic path that exits into the porous material. In some examples, the surgical implant device is a patient-specific device that is shaped to match the anatomy of a specific patient. A 3D printing process (such as a DMLS process or another 3D printing process), for example, may be used to manufacture the orthopedic surgical implant device based on images of the patient's anatomy.

One or more surfaces of the orthopedic surgical implant device may comprise a porous material that promotes bone ingrowth after implantation onto a patient's bone. This can help to secure the implanted device in the desired location and to promote long-term viability of the implant device. In some examples, the orthopedic surgical implant device may comprise a baseplate associated with an orthopedic implant, and the baseplate may include a top side and a back side. The top side may comprise a solid material (e.g., formed of titanium) and designed to receive an anatomical or reverse-anatomical element, such as glenoid plate (anatomical) or a glenoid sphere (reverse-anatomical). The bottom side of the baseplate may comprise a porous material (e.g., also formed of titanium) and the porous material may be configured to promote bone ingrowth after implantation onto a patient's bone. The porous material may be porous to fluid (e.g., water or a cleaning solution) whereas the solid material may be impervious to the fluid. In some examples, the orthopedic surgical implant device is a patient-specific and the bottom side that includes the porous material may define a surface that conforms to patient anatomy (e.g., the shape and contour of the patient's glenoid cavity in the patient's scapula bone).

In accordance with this disclosure, the one or more fluid channels are formed in the orthopedic surgical implant device to improve a post-manufacturing cleaning process. Fluid can be flushed into the channels in order to clean the orthopedic surgical implant device after it is manufactured. In response to the fluid passing through the one or more channels, the fluid exits the one or more fluid channels into the porous material of the orthopedic surgical implant device. In other words, the one or more channels define a fluidic path that exits into the porous material. In this way, the interior region of the orthopedic surgical implant device and the pores of the porous material can be more thoroughly cleaned, prior to use in a patient.

The one or more fluid channels may define one or more inlets for receiving fluid in the one or more channels. The one or more inlets may pass through one or more solid regions of the orthopedic surgical implant device. The one or more channels may pass through solid regions of the orthopedic surgical implant device and/or through porous regions. In any case, one or more outlets may deliver fluid from the one or more channels and into the porous material. Of course, if one or more of the channels themselves also pass though porous regions, then fluid may also enter the porous material out of the sidewalls of the channels (in addition to entering the porous material at the one or more outlets). The inlets and outlets may be one-to-one, one-to-many, or one-to-all. In other words, in some examples, there can be one inlet for every outlet, in some examples, there can be one or more inlets that each feed fluid to a plurality of outlets, and in some examples, there can be a single inlet that feeds fluid to a plurality of outlets. The inlet or inlets define a location for introducing fluid into the channels and the outlet or outlets define locations where fluid exits the channels into the porous material. In some examples, the inlets may be designed with one or for features that can mate with a nozzle for introducing fluid. In some examples, the outlets may be sized (relative to one another) to promote desirable fluid flow, such as by promoting equal or unequal fluid pressure out of different outlets.

FIG. 1 is a conceptual side view of an example orthopedic surgical implant device 100 consistent with this disclosure. Orthopedic surgical implant device 100 may comprise a body 102 that includes that includes a porous material 106 forming at least a portion of the body, wherein the porous material 106 is configured to promote bone ingrowth and is porous to a fluid. One or more fluid channels (e.g. channel 120) are formed in the body, such that in response to the fluid passing through channel 120, the fluid exits channel 120 into the porous material 106. In other words, the one or more channels 120 define a fluidic path that exits into porous material 106.

In the example of FIG. 1, the body 102 of orthopedic surgical implant device 100 includes a top surface 104 and a bottom surface 112. A top portion 105 of body 102 is formed of a solid material that is non-porous to fluid (such as water or a cleaning agent). The bottom portion of body 102, in contrast, is the portion that includes porous material 106 that is porous to the fluid. In the example of FIG. 1, an inlet 130 allows a fluid 140 to enter body 102 and pass through top portion 105 of body 102 and into one or more channels 120. In the example of FIG. 1, one or more channels 120 are formed in porous material 106, but it is also possible for all or part of channel 120 to be formed in top portion 105, which is solid and non-porous. Outlets 134 of channel 120 feed fluid 140 into porous material 106 in order to clean portion material 106 and to flush any residue or debris that may be present after the manufacturing process. Outlets 134 are shown as being within porous material 106 in FIG. 1, although they could also be formed in top portion 105 as long as they are still capable of feeding fluid into porous material 106. Upon injecting or directing fluid 140 into channel 120 via inlet 130, the fluid exits outlets 134 and may act like a shower that flushes through porous material 106. This inside-out cleaning process can improve the cleaning of any porous material within surgical implant device 100 relative to a conventional cleaning bath.

As noted, orthopedic surgical implant device 100 may comprise a baseplate, such as a baseplate associated with a glenoid implant. In this case, top surface 104 may be designed to receive another portion of a surgical implant, e.g., a glenoid plate or a glenoid sphere that is configured to be attached to top surface 104. Accordingly, top surface 104 may include features (not shown in FIG. 1) for receiving a glenoid plate or glenoid sphere, such as one or more fixation holes or fixation elements that allow a glenoid plate or glenoid sphere to be attached to top surface 104.

Top portion 105 may comprise a solid material that is non-porous in order to allow for robust attachment of top surface 104 to a glenoid plate or glenoid sphere. In the example of FIG. 1, the one or more fluid channels 120 pass through the solid material via inlet 130 to deliver fluid into channel 120, out of outlets 134, and into porous material 106. That is to say, the one or more outlets 134 are arranged to deliver the fluid from the one or more fluid channels 120 and into the porous material 106 of body 102. Body 102 (including the solid top portion 105 and the porous material 106 forming a bottom portion) may comprise titanium or another biocompatible material that is used for implants in the human body. FIG. 1 shows merely one example of fluid channels 120, which include one inlet 130 and a plurality of outlets 134 arranged to deliver fluid 140 and into porous material 106 at different locations. In other examples, inlets and outlets of one or more fluid channels may be one-to-one, one-to-many, or one-to-all. In other words, in some examples, there can be one inlet for every outlet, in some examples, there can be one or more inlets that each feed fluid to a plurality of outlets, and in some examples like FIG. 1, there can be a single inlet 130 that feeds fluid to a plurality of outlets 134. In some cases, there can be a plurality of inlets and a plurality of outlets, in which case there may be one inlet for every outlet, or possibly a plurality of outlets for some or all of the inlets.

In the example of FIG. 1, fluid channel 120 may define a ring-shaped channel through body 102. In this case, fluid channel 120 defines an inlet 130 to fluid channel 120 so that fluid can flow around the ring to a plurality of outlets 134 in order to deliver fluid 140 into the porous material 106 at different locations.

Bottom surface 112 may be defined to conform the patient-specific anatomy. To do so, orthopedic surgical implant device 100 may be created based on patient images (e.g., x-rays, radiograph images, magnetic resonance image (Mill) images, ultrasound images, endoscopic images, elastography, tactile imaging, thermography, medical photography, positron emission tomography, single-photon emission computed tomography, or other medical imaging). 3D modeling can be performed to define the shape of bottom surface 112 (and possibly other features or shapes of device 100) so that the orthopedic surgical implant device 100 matches patient anatomy, and 3D printing technology can be used to manufacture a patient-specific orthopedic surgical implant device 100. This can be especially useful to reduce or eliminate the need to resurface the patient's bone at the location of the implant. Some patients, for example, may have insufficient healthy bone surface to allow for reaming or other conditioning, making a precise fit of device 100 highly desirable for some patients (via a contoured bottom surface 112 that matches patient anatomy).

In the example of FIG. 1, orthopedic surgical implant device 100 includes a fixation pin 110 that extends from bottom surface 112 of body 102. In this example, fixation pin 102 includes both solid material 108 and porous material 107 that is designed to promote bone ingrowth. For example, fixation pin 110 may be inserted into a drilled hole in patient bone and orthopedic surgical implant device 100 can be pressed, screwed, or hammered into place such fixation pin 110 is inserted into patient bone and bottom surface 112 of body 102 is secured against the patent bone with a precise fit. In some cases, an additional screw or fixation element may be attached to fixation pin. In any case, bone ingrowth into porous material 106, 107 (after implantation) can help secure orthopedic surgical implant device 100 in place and promote long term fixation. With the example of shoulder arthroplasty, a glenoid plate (for an anatomical prosthetic) or a glenoid sphere (for reverse anatomical prosthetic) may be attached to top surface 104 of orthopedic surgical implant device 100 after the device is properly positioned in and on the patient's bone.

In the example of FIG. 1, fluid channel 120 defines a ring that is a fixed distance from a top surface 104 of the surgical implant device. In FIG. 1, the ring is formed in the porous material 106, but again, the ring could also be formed in top portion 105 that comprises a solid material, in which case outlets 134 would still deliver fluid to porous material 106. In other examples (not illustrated in FIG. 1), fluid channels could define ring that is a fixed distance from bottom surface 112 that conforms to patient specific anatomy, which may help deliver a more uniform amount of fluid to different regions of porous material 106 (e.g., as different regions of porous material 106 may have varied thicknesses). Also, the location and or size and shapes of outlets 134 may be defined to promote fluid delivery into porous material 106 in a desirable way. For example, the plurality of outlets 134 could have at least some different sizes to control fluid pressure out of the outlets, and locations of outlets 134 may be defined to promote uniform fluid delivery, e.g., possibly having more outlets in the thicker regions of porous material 106 (i.e. on the right side) and fewer outlets in thinner regions of porous material 106 (i.e., on the left side).

Fluid channels (such as fluid channel 120 of FIG. 1) may define uniform diameters or diameters that change to control fluid pressure for delivery of fluid to porous material. In some examples, the one or more fluid channels (e.g., fluid channel 120 of FIG. 1 or other fluid channels described herein) may define a diameter of greater than 0.7 millimeters to promote fluid delivery into porous material 106. The one or more fluid channels (e.g., fluid channel 120 of FIG. 1 or other fluid channels described herein) may define diameters that areas big or larger than the diameters of pores within porous material 106. If the pores are less than 0.7 millimeters, for example, the channels may be greater than 0.7 millimeters. At the same time, in some examples, the one or more fluid channels (e.g., fluid channel 120 or other fluid channels described herein) may define a diameter less than 1 millimeter to promote structural integrity of orthopedic surgical implant device 100. Other sizes of the fluid channels, however, may be desirable for other examples.

Figure 2:
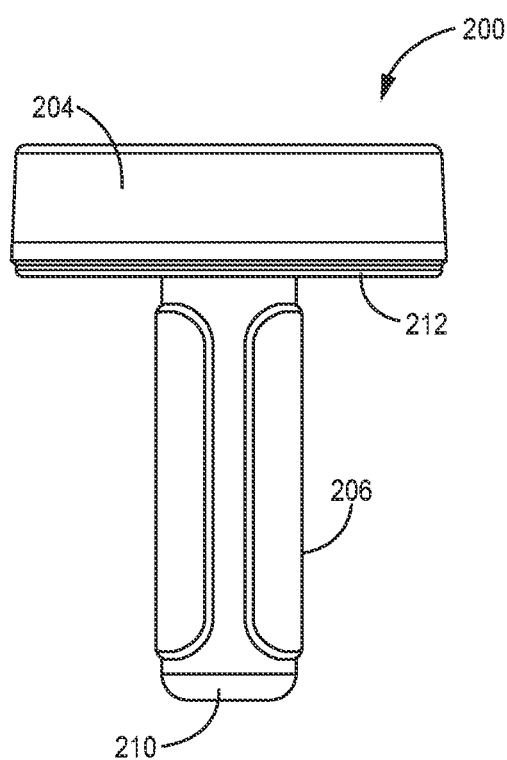
FIGS. 2 and 3 are side views of other example baseplates that may include fluid flush channels consistent with this disclosure.
Figure 3:
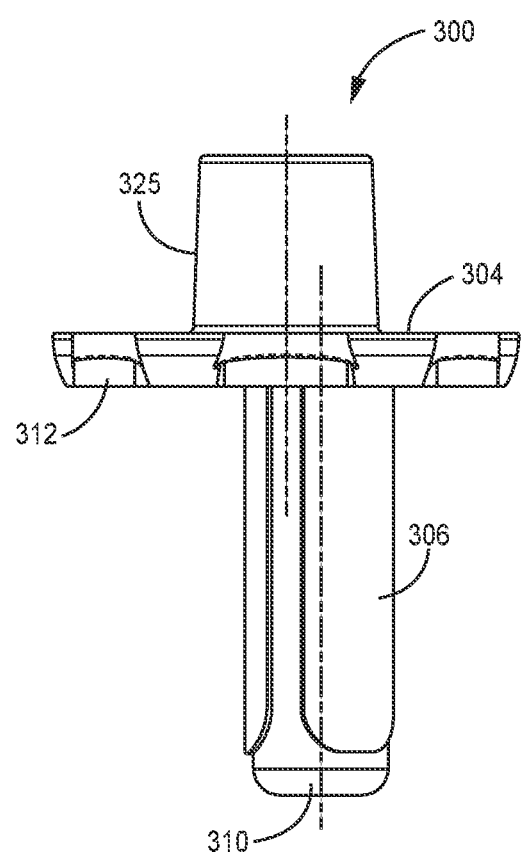

FIGS. 2 and 3 are side views of other example baseplates 200, 300 that may include fluid flush channels consistent with this disclosure. The fluid flush channels may be formed within the interiors of baseplates 200, 300 and are not illustrated in FIGS. 2 and 3. Baseplate 200 of FIG. 2 includes a top portion 204 that is nonporous to fluid. A top surface of top portion 204 may be adapted to receive a glenoid sphere, glenoid plate, or a prosthetic associated with another joint. For example, top surface of top portion 204 may be formed with a threaded hole for receiving a screw or fastener to attach a glenoid sphere, glenoid plate, or a prosthetic associated with another joint. Bottom portion 212 of baseplate 200 comprises a porous material. One or more fluid channels are formed within baseplate 200 so that fluid can be flushed through baseplate and into the porous material on bottom portion 212 of baseplate 200. A fixation pin 210 may extend from the bottom surface of baseplate 200 to allow baseplate 200 to be anchored into a patient's bone. A portion 206 of fixation pin 210 may comprise porous material, which like porous material 212, may be cleaned by fluid passing through one or more fluid channels within baseplate 200.

Baseplate 300 of FIG. 3 includes a top portion 304 that is nonporous to fluid. A top surface of top portion 404 may be adapted to receive a glenoid sphere, glenoid plate, or a prosthetic associated with another joint. In the example of FIG. 3, for example, baseplate 300 includes a protrusion 325 (which may be offset or centered relative to fixation pin 310). Protrusion 325, for example, may be adapted to receive a glenoid sphere, glenoid plate, or a prosthetic associated with another joint. In some examples, protrusion 325 may include a threaded hole for receiving a screw or fastener to attach a glenoid sphere, glenoid plate, or a prosthetic associated with another joint. In other examples, protrusion 325 may include a screw or other fixation elements for attaching to a glenoid sphere, glenoid plate, or a prosthetic associated with another joint.

Bottom portion 312 of baseplate 300 comprises at least some porous material. One or more fluid channels (not shown in FIG. 3) are formed within baseplate 300 so that fluid can be flushed through baseplate 300 and into the porous material on bottom portion 312 of baseplate 300. A fixation pin 310 may extend from the bottom surface of baseplate 300 to allow baseplate 300 to be anchored into a patient's bone. A portion 306 of fixation pin 310 may comprise porous material, which like porous material 312, may be cleaned by fluid passing through one or more fluid channels within baseplate 300.

Figure 4:
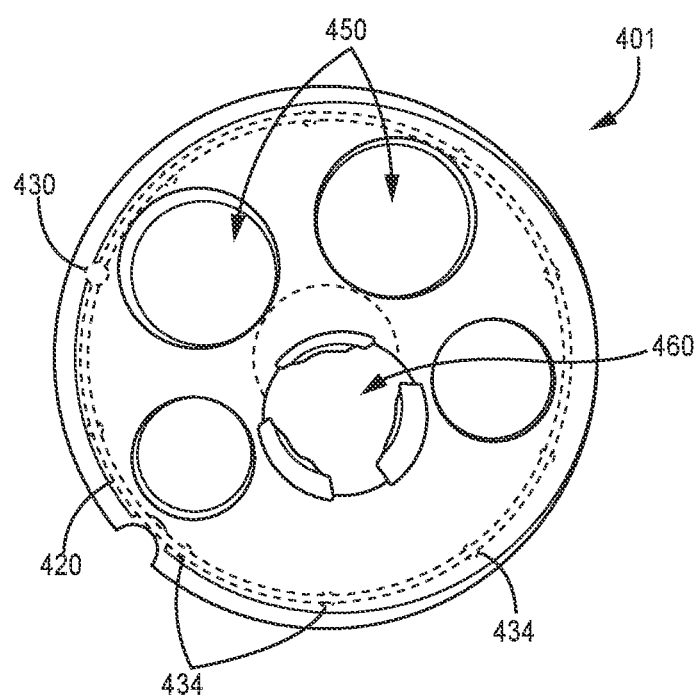
FIG. 4 is top view of the porous material portion of an example baseplate consistent with this disclosure.

FIG. 4 is top view of the porous material portion 401 of an example baseplate consistent with this disclosure. In this example, one or more fluid channels 420 are formed in the porous material portion 401 of the baseplate, although it is also possible for such fluid channels to be formed in a solid portion of the baseplate as long as the fluid channels feed fluid into the porous material portion of the baseplate. In the example of FIG. 4, an inlet 430 may receive fluid that passes through ring-shaped channel 420, out of outlets (e.g., outlets 434) and into the porous material. Element 460 may comprise a fixation hole adapted to receive a surgical prosthetic, such as glenoid plate, a glenoid sphere or a prosthetic associated with another joint. In addition, the baseplate (and thus the porous material portion 401 of the baseplate) may include a plurality of holes 450 for receiving screws or other fasteners to attach the surgical implant device to bone of a patient. The porous material (e.g., the bottom surface of portion 401) is arranged to contact the bone of the patient and to promote the bone ingrowth when the surgical implant device is attached to the bone via the screws that attach through holes 450.

Figure 5:
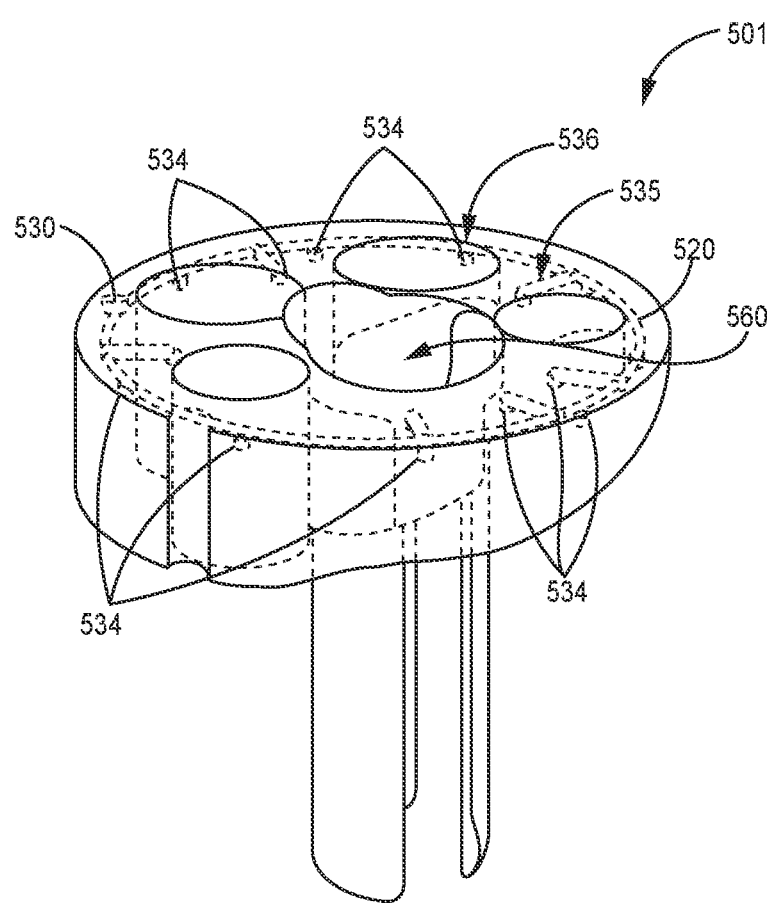
FIG. 5 is a perspective view of the porous material portion of another example baseplate consistent with this disclosure.

FIG. 5 is a perspective view of the porous material portion 501 of another example baseplate consistent with this disclosure. As shown, a ring-shaped fluid channel 520 passes though porous material portion 501 of the baseplate, although it is also possible for such fluid channels to be formed in a solid portion of the baseplate as long as the fluid channels feed fluid into the porous material portion of the baseplate. In the example of FIG. 5, an inlet 530 may receive fluid that passes through ring-shaped channel 520, out of outlets (e.g., outlets 534) and into the porous material. Element 560 may comprise a fixation hole adapted to receive a surgical prosthetic, such as glenoid plate, a glenoid sphere, or a prosthetic associated with another joint. In addition, the baseplate (and thus the porous material portion 401 of the baseplate) may include a plurality of holes (shown but not labeled in FIG. 5) for receiving screws to attach the surgical implant device to bone of a patient. In the example of FIG. 5, some of the outlets (e.g., outlet 536) are aligned below the ring-shaped channel 520 and some of the outlets (e.g., outlet 535) are offset from the ring-shaped channel and within an interior of the ring-shaped channel. In other examples, some outlets may be offset from the ring-shaped channel and be outside the interior of the ring-shaped channel. By including offset outlets (e.g., similar to outlet 535) fluid may be more evenly dispersed across the volume of porous material.

Figure 6:
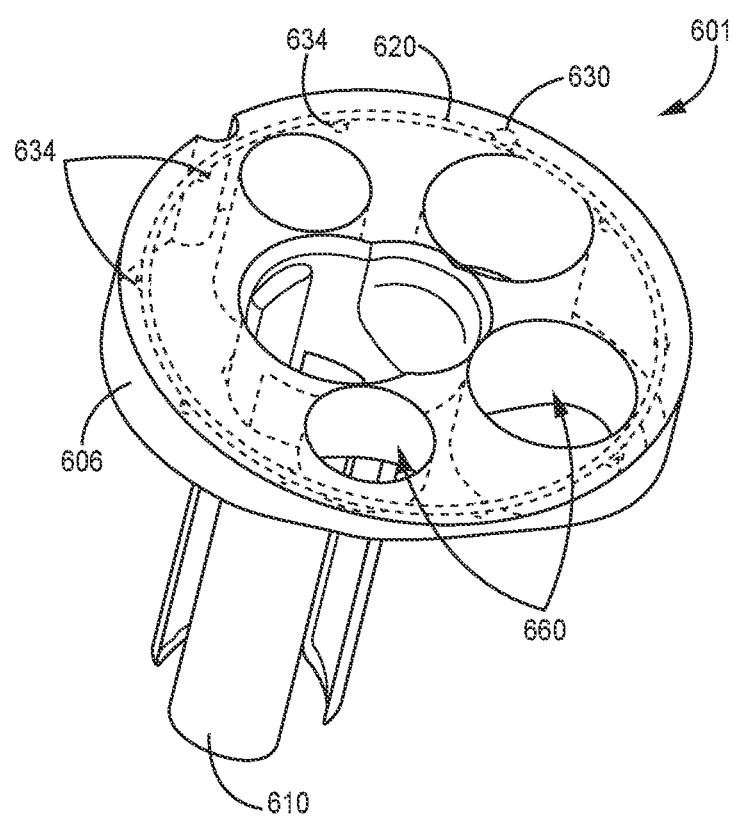
FIG. 6 is a perspective view of the porous material portion of another example baseplate consistent with this disclosure.

FIG. 6 is a perspective view of porous material portion 601 of an example baseplate consistent with this disclosure. In this example, one or more fluid channels 620 are formed in the porous material portion 601 of the baseplate, although it is also possible for such fluid channels to be formed in a solid portion of the baseplate as long as the fluid channels feed fluid into the porous material portion of the baseplate. In the example of FIG. 6, an inlet 630 may receive fluid that passes through ring-shaped channel 620, out of outlets (e.g., outlets 634) and into porous material 606. The porous material (e.g., the bottom surface of porous material 606) is arranged to contact the bone of the patient and to promote the bone ingrowth when the surgical implant device is attached to the bone of patient. Fixation holes 660 may be adapted to receive fixation screws for attaching to bone. A fixation pin 610 may be inserted into a hole formed in the patient's bone, and fixation pin 610 may also include porous material. Screws can then be attached through holes 660 to secure the baseplate at a desired location on the patient's bone.

Figure 7:
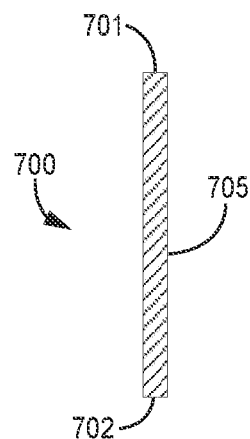
FIGS. 7-9 are conceptual illustrations of some examples of fluid flush channels that may be formed inside of a surgical implant device to facilitate the introduction of fluid into the interior of porous material of a surgical implant device.
Figure 8:
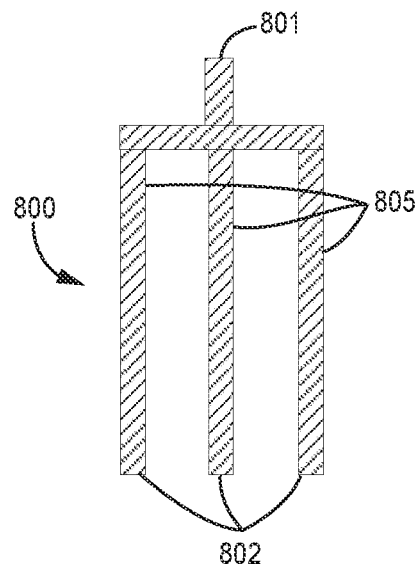
Figure 9:
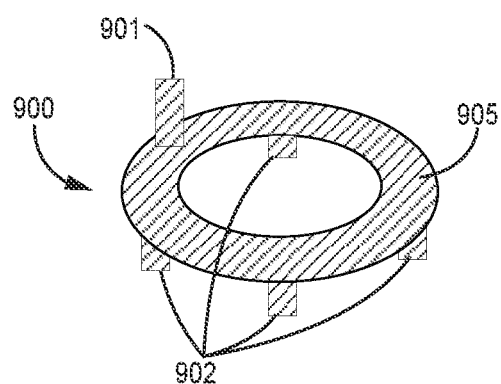

FIGS. 7-9 are conceptual illustrations of some examples of fluid flush channels that may be formed inside of an orthopedic surgical implant device to facilitate the introduction of fluid into the interior of porous material of the orthopedic surgical implant device. FIG. 7 shows an example fluid channel 700 comprising an inlet 701, an outlet 702, and a channel 705 that allows fluid to pass from inlet 701 though channel 705 and out of outlet 702. Channel 705 may be positioned within the interior of an orthopedic surgical implant device in order to deliver fluid to an interior of porous material for cleaning the porous material. To do so, outlet 702 may be positioned such that fluid exiting outlet 702 enters the porous material of an orthopedic surgical implant device. In this way, fluid channel 700 can be arranged inside an orthopedic surgical implant device so as to define a fluidic path that exits into the porous material of the orthopedic surgical implant device. The fluidic path is defined between inlet 701 and outlet 702. Channel 705 may pass through solid material and/or porous material of the orthopedic surgical implant device. Inlet 701 may be positioned on a top side, a side wall, or a bottom side of the orthopedic surgical implant device.

FIG. 8 shows an example fluid channel 800 comprising one inlet 801 and a plurality of outlets 802. A plurality of channels 805 for a channel network that allows fluid to pass from inlet 801 though channel channels 805 and out of the plurality of outlets 802. Channels 805 may be positioned within the interior of an orthopedic surgical implant device in order to deliver fluid to an interior of porous material for cleaning the porous material. To do so, outlets 802 may be positioned such that fluid exiting outlets 802 enters the porous material at different locations within an orthopedic surgical implant device. In this way, fluid channel 800 can be arranged in an orthopedic surgical implant device so as to define a fluidic path that exits into the porous material of the orthopedic surgical implant device. The fluidic path is defined between inlet 801 and outlets 802. Channels 805 may pass through solid material and/or porous material. Inlet 801 may be positioned on a top side, a side wall, or a bottom side of the orthopedic surgical implant device.

FIG. 9 shows an example fluid channel 900 comprising one inlet 901 and a plurality of outlets 902. A ring-shaped channel 905 allows fluid to pass from inlet 901 though channel 905 and out of the plurality of outlets 902. Channels 905 may be positioned within the interior of an orthopedic surgical implant device in order to deliver fluid to an interior of porous material for cleaning the porous material. To do so, outlets 902 may be positioned such that fluid exiting outlets 902 enters the porous material at different locations within an orthopedic surgical implant device. In this way, fluid channel 900 can be arranged in an orthopedic surgical implant device so as to define a fluidic path that exits into the porous material of the orthopedic surgical implant device. The fluidic path is defined between inlet 901 and outlets 902. Inlet 901 and ring-shaped channel 905 may pass through solid material and/or porous material. With the example of FIG. 9, inlet 901 is typically positioned on a top side of the orthopedic surgical implant device, although the inlet could also be positioned in other locations, such as a side wall, or a bottom side of the orthopedic surgical implant device.

FIGS. 7-9 are merely exemplary. In other examples, the channel or channels could define a wide variety of shapes or configurations, including star-shapes, square shapes, polygon shapes, elliptical shapes, a network or networks of channels, shapes that match or conform to the shape of any particular implant, shapes that match or conform to porous material portions of any particular implant, or other shapes. Also, the inlets and outlets may include features to promote fluid delivery. For example, inlets 701, 801, 901 may be designed with one or for features that can mate with a nozzle for introducing fluid, such as notches, grooves or tapers for mating with corresponding shapes or features of a nozzle used for introducing fluid to channels 705, 805, 905. Also, outlets 702, 802, 902 may be sized to promote desirable fluid flow, such as by promoting equal or unequal fluid pressure out of different outlets when the device includes a plurality of outlets (and either one inlet or a plurality of inlets).

Figure 10:
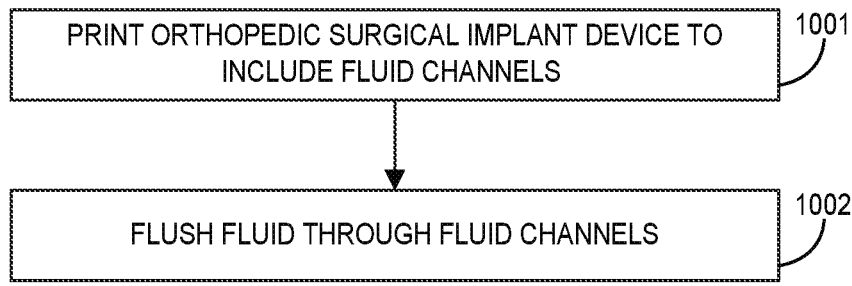
FIGS. 10 and 11 are flow diagrams showing some example methods consistent with this disclosure.
Figure 11:
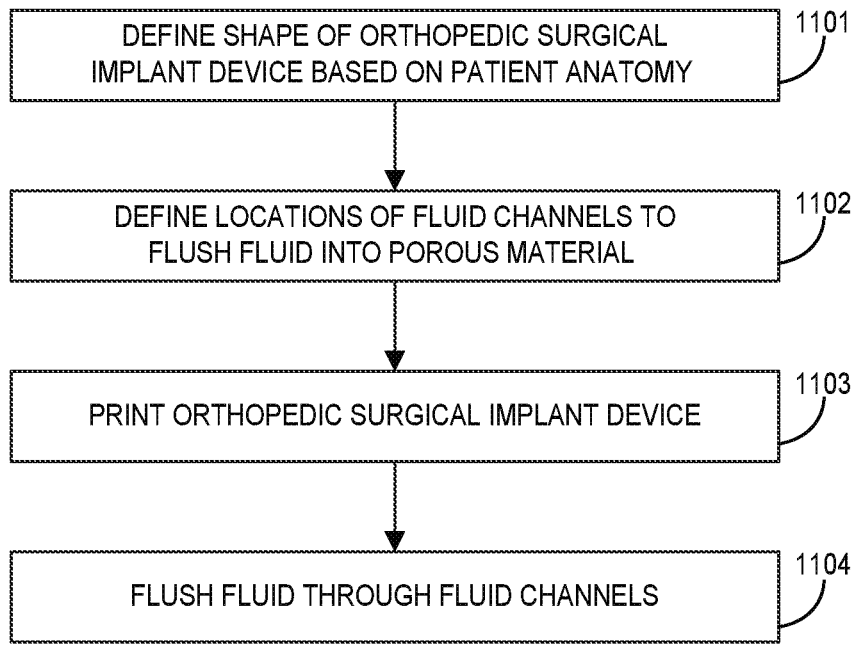

FIGS. 10 and 11 are flow diagrams showing some example methods consistent with this disclosure. As shown in FIG. 10, a process of creating an orthopedic surgical implant device may include printing the orthopedic surgical implant device to include fluid channels (1001). Printing the orthopedic surgical implant device, for example, may involve a 3D printing process such as such as a direct metal laser sintering (DMLS) process. In some cases, the size and shape of the orthopedic surgical implant device may be based on images of the patient's anatomy. By using 3D printing technology, the shape of orthopedic surgical implant device can be made to match patient anatomy, which can improve the outcome for some patients. After printing the orthopedic surgical implant device (1001), fluid is flushed through the fluid channels (1002) to clean the orthopedic surgical implant device. This inside-out cleaning process of flushing fluid into the channels can improve the cleaning of any porous material within the orthopedic surgical implant device relative to a conventional cleaning bath. In some cases, flushing fluid through the channels (1002) may help to remove any residue or debris that may be present after the 3D printing process.

In some orthopedic surgical procedures, a surgeon may implant one or more implant devices in a patient. The implant devices may be available in several different standard shapes, styles, and sizes. The surgeon may select a particular prosthetic device (e.g., a particular shape, style, and/or size) to implant based on various characteristic of the patient. The surgeon may perform various steps to prepare the patient's bone to receive the implant device. These steps may include removal of portions of the bone (e.g., via reaming) in order to create a surface of the bone that matches a surface of the implant device. Matching surfaces between the bone and the implant device may provide for better patient outcomes (e.g., as the implant device may have a better fit with the bone and be more solidly affixed to the bone). However, in some examples, it may be desirable to minimize, or eliminate, the need to remove portions of a bone to prepare the bone to receive an implant device. For instance, patients who undergo an orthopedic surgical procedure may have limited healthy bone available.

A system (e.g., a surgical planning system) may facilitate the designing of patient specific implant devices. For instance, the system may obtain a three-dimensional (3D) model of a bone of the patient (e.g., generated based on images of the bone, such as x-ray or magnetic resonance imaging (MM) images), and a template model of an implant device (e.g., a computer-aided design (CAD) model of the implant device). The system may generate a model of a patient specific implant device based on the 3D model of the bone and the template model of the implant device. For instance, the system may generate the model of a patient specific implant device such that a surface of the patient specific implant device matches a surface of the bone. These or other steps may be performed in the process of printing orthopedic surgical implant device (1001). Moreover, as part of the design process, fluid channels can also be designed to promote desirable fluid flushing (1002) after the 3D printing process.

The system may output the generated model for manufacturing via the printing process. For instance, the system may output the model to be manufactured into a physical patient specific implant device that a surgeon may subsequently implant into the patient. In this way, the system may facilitate the design of patient specific implant devices, and as described herein, fluid channels may be used in the design to allow for a desirable post-printing fluid flush through porous material of the device (1002).

The techniques of this disclosure are described below with respect to a shoulder arthroplasty surgical procedure. Examples of shoulder arthroplasties include, but are not limited to, reversed arthroplasty, augmented reverse arthroplasty, standard total shoulder arthroplasty, augmented total shoulder arthroplasty, and hemiarthroplasty. However, the techniques are not so limited. As mentioned, the fluid flushing channels described herein may be useful for a wide variety of surgical implant devices, including base plates or prosthetic devices associated with other joints.

A typical shoulder arthroplasty includes various work on a patient's scapula and performing various work on the patient's humerus. The work on the scapula may generally be described as preparing the scapula (e.g., the glenoid cavity of the scapula) for attachment of a prosthesis and attaching the prosthesis to the prepared scapula. Similarly, the work on the humerus may generally be described as preparing the humerus for attachment of a prosthesis and attaching the prosthesis to the prepared humerus. As described herein, orthopedic implant devices for the scapula or the humerus may include fluid channels for flushing fluid through porous material after manufacturing the devices. Also, the fluid flushing channels described herein may be useful for a wide variety of surgical implant devices, including base plates or prosthetic devices associated with other joints In an example surgical technique, the work steps associated with a surgical procedure may include resection of a humeral head, creating a pilot hole, sounding, punching, compacting, surface preparation, with respect to the humerus, and attaching an implant to the humerus. Additionally, in some techniques, the work steps may include bone graft work steps, such as installation of a guide in a humeral head, reaming of the graft, drilling the graft, cutting the graft, and removing the graft, e.g., for placement with an implant for augmentation of the implant relative to a bone surface such as the glenoid.

In performing a shoulder arthroplasty, in some cases, a surgeon may perform one or more steps to expose a patient's humerus. For instance, the surgeon may make one or more incisions to expose the upper portion of the humerus including the humeral head. The surgeon may position one or more retractors to maintain the exposure. In some examples, a mixed-realty system may provide guidance to assist in the exposure of the humerus, e.g., by making incisions, and/or placement of retractors. Many different techniques may be used to prepare a scapula for prosthesis attachment and to perform actual prosthesis attachment. Regardless of the technique used, it may be desirable to build orthopedic implant devices with fluid flush channels to help improve the cleaning of such devices after manufacture.

In some example techniques, the surgical procedure steps include installation of a guide in a glenoid of the scapula, reaming the glenoid, creating a central hole in the glenoid, creating additional anchorage positions in the glenoid, and attaching an implant to the prepared glenoid. As a guide pin is used, the example technique may be considered a cannulated technique. However, the techniques and devices of this disclosure are applicable to non-cannulated techniques.

A surgeon may also perform one or more steps to expose a patient's glenoid. For instance, with the patient's arm abducted and internally rotated, the surgeon may make one or more incisions to expose the glenoid. The surgeon may position one or more retractors to maintain the exposure. In some examples, a mixed reality system may provide guidance to assist in the exposure and/or placement of retractors. Again, the orthopedic surgical devices described herein with fluid flush channels to facilitate cleaning may help to improve surgical outcomes by providing a way to more thoroughly clean porous material of orthopedic surgical devices, which is desirable.

FIG. 11 is another flow diagram showing a method consistent with this disclosure. As shown in FIG. 11, a process of creating an orthopedic surgical implant device may include defining a shape of an orthopedic surgical implant device based on patient anatomy (1101). For example, one or more shapes or surfaces of an orthopedic surgical implant device may be defined or selected based on patient images (e.g., x-rays, radiograph images, MM images, ultrasound images, endoscopic images, elastography, tactile imaging, thermography, medical photography, positron emission tomography, single-photon emission computed tomography, or other medical imaging). 3D modeling can be performed to define the shape of bottom surface (e.g., surface 112 of device 100 FIG. 1 and possibly other features or shapes of device 100) so that the orthopedic surgical implant device matches patient anatomy. Some patients, for example, may have insufficient healthy bone surface to allow for reaming or other conditioning, making a precise fit of an orthopedic surgical implant device highly desirable for some patients (e.g., via a contoured bottom surface (such as surface 112 of FIG. 1) that matches patient anatomy).

In some cases, a system (e.g., a surgical planning system) may facilitate the designing of patient specific implant devices or otherwise define the shape of an orthopedic surgical implant device (1101). For instance, the system may obtain a 3D model of a bone of the patient (e.g., generated based on images of the bone, such as x-ray or magnetic resonance imaging (MM) images), and a template model of an implant device (e.g., a computer-aided design (CAD) model of the implant device). The system may generate a model of a patient specific implant device based on the 3D model of the bone and the template model of the implant device. For instance, the system may generate the model of a patient specific implant device such that a surface of the patient specific implant device matches a surface of the bone. These or other steps may be performed to define the shape of an orthopedic surgical implant device (1101).

The system or designer may then define locations of fluid channels (1102). In particular, the fluid channels can be defined within the interior of the orthopedic surgical implant device as shown herein. This may involve designing the size, shape, and location of one or more fluid channels in way that promotes the ability to clean the interior of the pores of porous material. The channels may be defined to promote the introduction of fluid, but the channels may also be designed to promote structural integrity of the device. Accordingly, fluid channels may be sized with diameters greater than 0.7 millimeters but less than or equal to one millimeter to help ensure both promote the introduction of fluid while also promoting structural integrity of the device. The size, shape, and design of the fluid channels may be different in various cases, and in some cases, the size, shape, and design of the fluid channels may be at least partially based on the shape of the patient-specific device. Moreover, in some cases, the size, shape, and design of the fluid channels may be based on the patient's anatomy.

Upon defining the shape of the orthopedic implant device (1101) and defining locations of fluid channels (1102), a method may include printing the orthopedic surgical implant device to include fluid channels (1103). Printing the orthopedic surgical implant device, for example, may involve a 3D printing process such as such as a direct metal laser sintering (DMLS) process. By using 3D printing technology, the shape of orthopedic surgical implant device can be made to match patient anatomy and made with fluid channels, which can improve the ability to clean the patient-specific device and possibly improve the outcome for some patients. After printing the orthopedic surgical implant device (1103), fluid is flushed through the fluid channels (1104) to clean the orthopedic surgical implant device. In particular, fluid is flushed thought a fluidic path defined by the channels that exits into the porous material of the orthopedic surgical implant device. This inside-out cleaning process of flushing fluid into the channels can improve the cleaning of any porous material within the orthopedic surgical implant device relative to a conventional cleaning bath. Again, in some cases, flushing fluid through the channels (1102) may help to remove any residue or debris that may be present after the 3D printing process.

Figure 12:
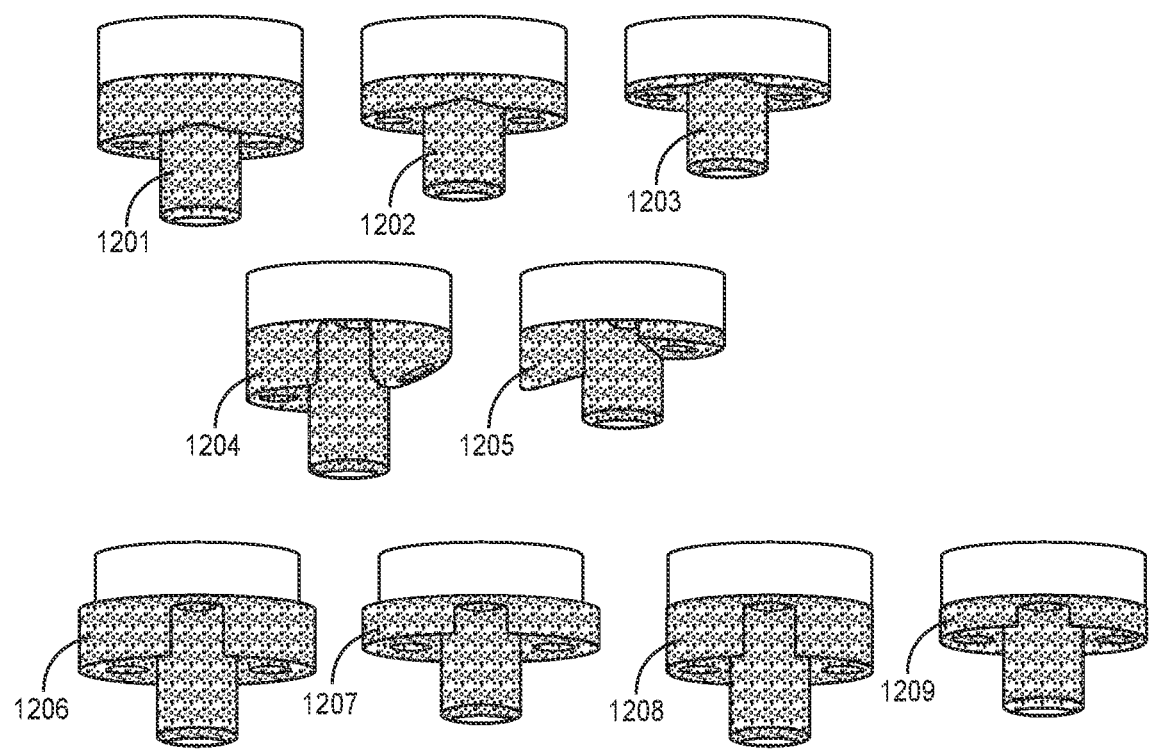
FIG. 12 is a perspective view of variety of different baseplates having different sizes and shapes of porous material.

FIG. 12 is a perspective view of variety of different baseplates having different sizes and shapes of porous material. In particular, the bottom portions of baseplates 1201, 1202, 1203, 1204, 1205, 1206, 1207, 1208, and 1209 are all slightly different so as to conform to patient anatomy or to provide different shapes of the porous material that may be better suited for different patient scenarios. Each of baseplates 1201, 1202, 1203, 1204, 1205, 1206, 1207, 1208, and 1209 may include one or more fluid flush channels, as described herein, to promote cleaning.

Figure 13:
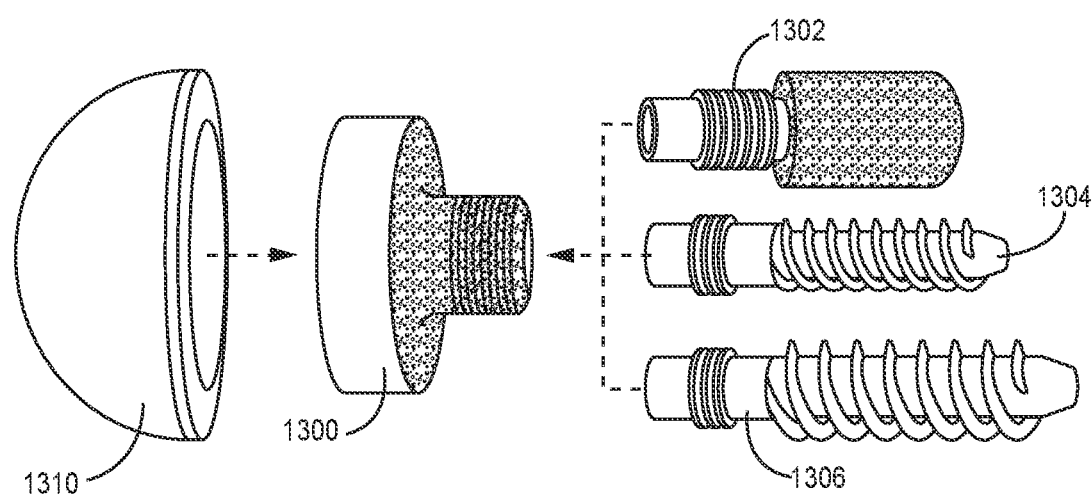
FIG. 13 is a perspective exploded view showing a baseplate, different screws that can be attached to the baseplate, and an example glenoid sphere that can be attached to the baseplate.

FIG. 13 is a perspective exploded view showing a baseplate 1300, different fixation elements 1302, 1304 or 1306 that can be attached to baseplate 1300, and an example glenoid sphere 1310 that can be attached to baseplate 1300. Baseplate 1300 is one example of an orthopedic surgical implant device that can be designed and printed with one or more fluid flush channels to promote cleaning of porous material. Also, fixation element 1302 is another example of an orthopedic surgical implant device that can be designed and printed with one or more fluid flush channels to promote cleaning of porous material. Baseplate 1300 may define a top surface configured to receive glenoid sphere 1310, such as via a screw hole. A bottom surface of baseplate 1300 is configured to interact with bone of a patent and promote bone ingrowth, and the porous material is exposed on the bottom surface of baseplate 1300.

Figure 14:
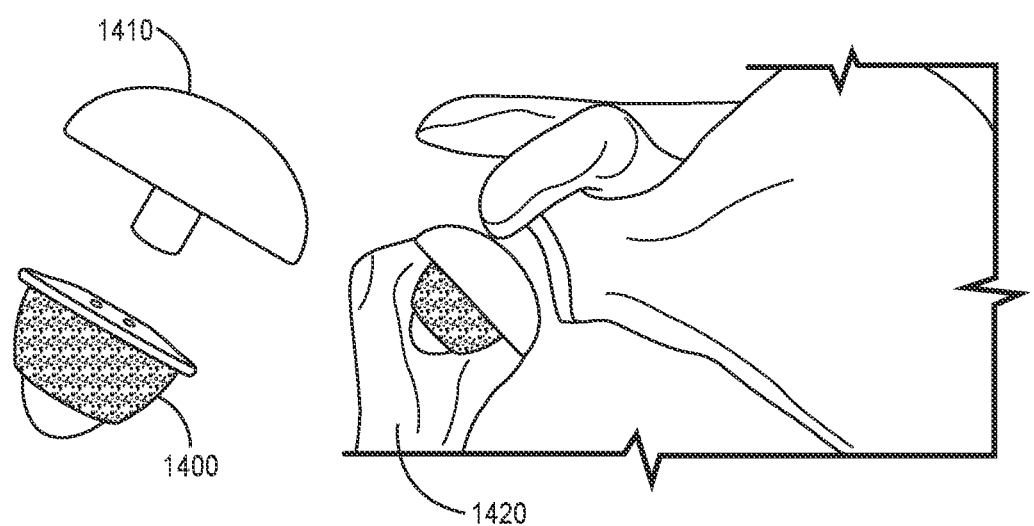
FIG. 14 is perspective conceptual view showing another type of shoulder implant device that includes a baseplate may use fluid channels as described herein.

FIG. 14 is perspective conceptual view showing another type of shoulder implant device that includes a baseplate may use fluid channels as described herein. In particular, device 1400 may comprise a baseplate designed for implantation on a humeral head of a patient's humerus 1420. A prosthetic humeral head 1410 may attach to device 1400. As described herein, device 1400 is another type of baseplate that could use fluid flush channels for flushing fluid into porous material for cleaning purposes.

In still other examples, the fluid flush channels described in this disclosure could be used any a wide a variety of other orthopedic surgical implant devices, such as anatomical or revers anatomical devices associated with any joint, including shoulders, fingers, thumbs, toes, knees, hips, elbows, or any joint. The fluid flush channels are especially useful for patient-specific baseplates or other implants that are designed to match patient anatomy, are 3D printed, and include porous material to promote bone ingrowth. However, the fluid flush channels may also be added to non-patent specific devices or devices that are created or formed in other ways.

The following examples demonstrate various features of this disclosure.

Example 1—A surgical implant device comprising: a body comprising a porous material forming at least a portion of the body, wherein the porous material is configured to promote bone ingrowth and is porous to a fluid; and one or more fluid channels formed in the body, wherein the one or more channels define a fluidic path that exits into the porous material.

Example 2—The surgical implant device of example 1, wherein the surgical implant device comprises a baseplate associated with an orthopedic surgical implant.

Example 3—The surgical implant device of example 2, wherein the baseplate is associated with a glenoid implant, the surgical implant device further comprising: a glenoid plate or a glenoid sphere configured to be attached to the baseplate.

Example 4—The surgical implant device of any combination of examples 1-3, wherein the body further comprises a solid material that is non-porous, wherein at least a portion of the one or more fluid channels pass through the solid material.

Example 5—The surgical implant device of any combination of examples 1-4, wherein the body is formed of titanium.

Example 6—The surgical implant device of any combination of examples 1-5, wherein the one or more fluid channels include one or more inlets configured to receive the fluid that flushes through the one or more fluid channels and into the porous material.

Example 7—The surgical implant device of any combination of examples 1-6, wherein the one or more fluid channels include a one or more outlets arranged to deliver the fluid from the one or more fluid channels and into the porous material.

Example 8—The surgical implant device of any combination of examples 1-5, wherein the fluid channels define an inlet for receiving fluid, and a plurality of outlets arranged to deliver the fluid and into the porous material at different locations.

Example 9—The surgical implant device of any combination of examples 1-8, wherein the one or more fluid channels define a ring-shaped channel through the body.

Example 10—The surgical implant device of any combination of example 1-9, wherein the one or more fluid channels define an inlet to the ring-shaped channel and a plurality of outlets from the ring-shaped channel arranged to deliver the fluid into the porous material at different locations.

Example 11—The surgical implant device of any combination of examples 1-10, wherein some of the outlets are aligned below the ring-shaped channel and some of the outlets are offset from the ring-shaped channel and within an interior of the ring-shaped channel.

Example 12—The surgical implant device of any combination of examples 1-11, wherein the fluid channels include a plurality of inlets for receiving a fluid and a plurality of outlets for delivering the fluid into the porous material.

Example 13—The surgical implant device of any combination of examples 1-12, wherein the surgical implant device includes a plurality of holes for receiving screws to attach the surgical implant device to bone of a patient, wherein the porous material is arranged to contact the bone and to promote the bone ingrowth when the surgical implant device is attached to the bone.

Example 14—The surgical implant device of any combination of examples 1-13, wherein the surgical implant device includes: a top surface configured to receive a glenoid plate or a glenoid sphere; and a bottom surface configured to interact with bone of a patent and promote bone ingrowth, wherein the porous material is exposed on the bottom surface.

Example 15—The surgical implant device of any combination of examples 1-14, further comprising a fixation pin, wherein the fixation pin extends from the bottom surface.

Example 16—The surgical implant device of example 15, wherein the fixation pin includes at least some of the porous material.

Example 17—The surgical implant device of any combination of examples 1-16, wherein the surgical implant device is formed by a 3D printing process.

Example 18—The surgical implant device of any combination of examples 1-17, wherein the one or more fluid channels define a diameter of greater than 0.7 millimeters to promote fluid delivery into the porous material.

Example 19—The surgical implant device of any combination of examples 1-18, wherein the diameter of the one or more fluid channels is less than or equal to one millimeter to promote structural integrity of the surgical implant device.

Example 20—The surgical implant device of any combination of examples 1-19, wherein the one or more fluid channels define a ring that is a fixed distance from a top surface of the surgical implant device.

Example 21—The surgical implant device of example 20 or 22, wherein the ring is formed in the porous material.

Example 22—The surgical implant device of any combination of examples 1-20, wherein the one or more fluid channels define a ring that is a fixed distance from a bottom surface of the surgical implant device, wherein the bottom surface conforms to patent-specific anatomy.

Example 23—The surgical implant device of any combination of examples 1-22, wherein the body further comprises a solid material that is non-porous and wherein the surgical implant device includes: a top surface configured to receive a glenoid plate or a glenoid sphere, the top surface comprising at least some of the solid material; and a bottom surface configured to interact with bone of a patent and promote bone ingrowth, wherein at least some of the porous material is exposed on the bottom surface, and wherein the one or more fluid channels include one or more inlets for passing fluid through the top surface and into the one or more fluid channels, and a plurality of outlets arranged to deliver fluid from the fluid channels and into the porous material.

Example 24—The surgical implant device of any combination of examples 1-23, wherein the one or more fluid channels include one or more inlets for passing fluid through the top surface and into the one or more fluid channels, and a plurality of outlets arranged to deliver fluid from the fluid channels and into the porous material wherein the plurality of outlets have at least some different sizes to control fluid pressure out of the outlets.

Example 25—A method comprising: printing a surgical implant device comprising: a body including a porous material forming at least a portion of the body, wherein the porous material is configured to promote bone ingrowth and is porous to a fluid, and one or more fluid channels formed in the surgical implant device, wherein the one or more channels define a fluidic path that exits into the porous material.

Example 26—The method of example 25, the method further comprising: flushing fluid into the one or more fluid channels and into the porous material.

Example 27—The method of example 25 or 26, the method further comprising defining one or more patient-specific features into the body.

Example 28—The method of any combination of examples 25-27, the method further comprising defining locations of the one or more fluid channels based at least in part on the one or more patient-specific features.

Example 29—The method of any combination of examples 25-28, wherein the surgical implant device comprises a baseplate for a surgical implant that includes at least some solid material and the porous material.

Example 30—The method of any combination of examples 25-29, wherein the baseplate comprises a baseplate for a glenoid implant, the method further comprising: printing the baseplate to define a top surface configured to receive a glenoid plate or a glenoid sphere, the top surface comprising at least some of the solid material; printing the baseplate to define a bottom surface configured to interact with bone of a patent and promote bone ingrowth, wherein at least some of the porous material is exposed on the bottom surface; printing the baseplate to include the one or more fluid channels; printing the baseplate to include one or more inlets for passing fluid through the top surface and into the one or more fluid channels; and printing the baseplate to include a plurality of outlets arranged to deliver fluid from the fluid channels and into the porous material.

Example 31—The method of any combination of examples 25-30, the method further comprising: printing the baseplate to include a fixation pin that extends from the bottom surface, wherein the fixation pin includes at least some of the porous material.

Example 32—The method any combination of examples 25-31, wherein printing the surgical implant device comprises printing the surgical implant device using a direct metal laser sintering (DMLS) process.

Example 33—The method of any combination of examples 25-32, wherein printing the surgical implant device comprises printing the surgical implant device out of titanium.

These and other examples are described by the following claims.

The invention claimed is:

1. A surgical implant device comprising:
    a body comprising a top portion formed of a solid material that is non-porous and a bottom portion formed of a porous material, wherein the porous material is configured to promote bone ingrowth and is porous to a fluid; and
    one or more fluid channels formed in the body, wherein at least a portion of the one or more fluid channels pass through the solid material of the top portion of the body and wherein the one or more channels define a fluidic path that exits into the porous material,
    wherein the one or more fluid channels include a ring-shaped channel through the body, and
    wherein the one or more fluid channels define an inlet to the ring-shaped channel and a plurality of outlets from the ring-shaped channel arranged to deliver the fluid into the porous material at different locations.

2. The surgical implant device of claim 1, wherein the surgical implant device comprises a baseplate associated with an orthopedic surgical implant.

3. The surgical implant device of claim 2, wherein the orthopedic surgical implant comprises a glenoid implant and the baseplate is associated with the glenoid implant, the surgical implant device further comprising:
    a glenoid plate or a glenoid sphere configured to be attached to the baseplate.

4. The surgical implant device of claim 1, wherein the body is formed of titanium.

5. The surgical implant device of claim 1, wherein some of the outlets are aligned below the ring-shaped channel and some of the outlets are offset from the ring-shaped channel.

6. The surgical implant device of claim 1, wherein the fluid channels include a plurality of inlets for receiving a fluid and a plurality of outlets for delivering the fluid into the porous material.

7. The surgical implant device of claim 1, wherein the surgical implant device includes a plurality of holes for receiving screws to attach the surgical implant device to bone of a patient, wherein the porous material is arranged to contact the bone and to promote the bone ingrowth when the surgical implant device is attached to the bone.

8. The surgical implant device of claim 1, wherein the surgical implant device includes:
    a top surface configured to receive a glenoid plate or a glenoid sphere; and
    a bottom surface configured to interact with bone of a patent and promote bone ingrowth, wherein the porous material is exposed on the bottom surface.

9. The surgical implant device of claim 8, further comprising a fixation pin, wherein the fixation pin extends from the bottom surface.

10. The surgical implant device of claim 9, wherein the fixation pin includes at least some of the porous material.

11. The surgical implant device of claim 1, wherein the surgical implant device is formed by a 3D printing process.

12. The surgical implant device of claim 1, wherein the one or more fluid channels define a diameter of greater than 0.7 millimeters to promote fluid delivery into the porous material.

13. The surgical implant device of claim 12, wherein the diameter of the one or more fluid channels is less than or equal to one millimeter to promote structural integrity of the surgical implant device.

14. The surgical implant device of claim 1, wherein the ring-shaped channel is a fixed distance from a top surface of the surgical implant device.

15. The surgical implant device of claim 1, wherein the ring-shaped channel is formed in the porous material.

16. The surgical implant device of claim 1, wherein the ring-shaped channel is a fixed distance from a bottom surface of the surgical implant device, wherein the bottom surface conforms to patient-specific anatomy.

17. The surgical implant device of claim 1, wherein the surgical implant device includes:
- a top surface configured to receive a glenoid plate or a glenoid sphere, the top surface comprising at least some of the solid material; and
- a bottom surface configured to interact with bone of a patient and promote bone ingrowth, wherein at least some of the porous material is exposed on the bottom surface.

18. The surgical implant device of claim 1, wherein the plurality of outlets have at least some different sizes to control fluid pressure out of the outlets.

19. A method comprising:
printing a surgical implant device comprising:
- a body including a top portion formed of a solid material that is non-porous and a bottom portion formed of a porous material, wherein the porous material is configured to promote bone ingrowth and is porous to a fluid, and
- one or more fluid channels formed in the surgical implant device, wherein at least a portion of the one or more fluid channels pass through the solid material of the top portion of the body and wherein the one or more channels define a fluidic path that exits into the porous material,
wherein the one or more fluid channels include a ring-shaped channel through the body, and
wherein the one or more fluid channels define an inlet to the ring-shaped channel and a plurality of outlets from the ring-shaped channel arranged to deliver the fluid into the porous material at different locations.

20. The method of claim 19, the method further comprising:
flushing fluid into the one or more fluid channels and into the porous material.

21. The method of claim 19, the method further comprising defining one or more patient-specific features for the body to conform to a patient-specific anatomy.

22. The method of claim 21, the method further comprising defining locations of the one or more fluid channels based at least in part on the one or more patient-specific features.

23. The method of claim 19, wherein the surgical implant device comprises a baseplate.

24. The method of claim 23, wherein the baseplate is for a glenoid implant, the method further comprising:
printing the baseplate to define a top surface configured to receive a glenoid plate or a glenoid sphere, the top surface comprising at least some of the solid material;
printing the baseplate to define a bottom surface configured to interact with bone of a patient and promote bone ingrowth, wherein at least some of the porous material is exposed on the bottom surface;
printing the baseplate to include the one or more fluid channels;
printing the baseplate to include the inlet; and
printing the baseplate to include the plurality of outlets.

25. The method of claim 24, the method further comprising:
printing the baseplate to include a fixation pin that extends from the bottom surface, wherein the fixation pin includes at least some of the porous material.

26. The method of claim 19, wherein printing the surgical implant device comprises printing the surgical implant device using a direct metal laser sintering (DMLS) process.

27. The method of claim 19, wherein printing the surgical implant device comprises printing the surgical implant device out of titanium.

* * * * *